(12) United States Patent
Pujol Ramo et al.

(10) Patent No.: US 9,750,406 B2
(45) Date of Patent: Sep. 5, 2017

(54) METHOD FOR THE DETECTION OF VISUAL FUNCTION LOSSES

(71) Applicant: UNIVERSITAT POLITÉCNICA DE CATALUNYA, Barcelona (ES)

(72) Inventors: Jaume Pujol Ramo, Barcelona (ES); Juan Carlos Ondategui Parra, Barcelona (ES); Maritxell Vilaseca Ricart, Barcelona (ES); Montserrat Arjona Carbonell, Barcelona (ES); Rosa Borrás Garcia, Barcelona (ES)

(73) Assignee: UNIVERSITAT POLITECNICA DE CATALUNYA, Barcelona (ES)

( * ) Notice: Subject to any disclaimer, the term of this patent is extended or adjusted under 35 U.S.C. 154(b) by 17 days.

(21) Appl. No.: 14/398,976

(22) PCT Filed: May 3, 2013

(86) PCT No.: PCT/ES2013/070275
§ 371 (c)(1),
(2) Date: Nov. 4, 2014

(87) PCT Pub. No.: WO2013/164509
PCT Pub. Date: Nov. 7, 2013

(65) Prior Publication Data
US 2015/0103314 A1    Apr. 16, 2015

(30) Foreign Application Priority Data

May 4, 2012 (ES) .................. 201230673

(51) Int. Cl.
*A61B 3/00* (2006.01)
*A61B 3/12* (2006.01)
*A61B 3/103* (2006.01)
*A61B 3/117* (2006.01)
*A61B 3/13* (2006.01)
*A61B 3/14* (2006.01)
*A61B 3/028* (2006.01)
*A61B 3/10* (2006.01)

(52) U.S. Cl.
CPC ............. *A61B 3/12* (2013.01); *A61B 3/0025* (2013.01); *A61B 3/028* (2013.01); *A61B 3/103* (2013.01); *A61B 3/117* (2013.01); *A61B 3/13* (2013.01); *A61B 3/14* (2013.01); *A61B 3/102* (2013.01)

(58) Field of Classification Search
CPC .... A61B 3/12; A61B 3/13; A61B 3/14; A61B 3/102; A61B 3/103; A61B 3/117
USPC .................................................. 351/206, 246
See application file for complete search history.

(56) References Cited

U.S. PATENT DOCUMENTS

| 8,488,851 | B2 | 7/2013 | Artal Soriano et al. |
| 2008/0018855 | A1 | 1/2008 | Larichev et al. |
| 2010/0195876 | A1 | 8/2010 | Artal Soriano et al. |

FOREIGN PATENT DOCUMENTS

| ES | 2265225 A1 | 2/2007 |
| ES | 2391192 A1 | 11/2012 |
| WO | WO 2008135618 A1 | 11/2008 |
| WO | WO 2013/164509 A1 | 11/2013 |

*Primary Examiner* — Jack Dinh
(74) *Attorney, Agent, or Firm* — Robert J. Hess; Hess Patent Law Firm

(57) ABSTRACT

The invention relates to a method for the detection of visual function losses. The method comprises analysing the optical quality of a patient's eye based on one or more retinal images thereof or based on information relating to retinal images corresponding to an eye having an anterior segment and intraocular means that are healthy. The method comprises: detecting a visual function loss of the visual system of functional or pathological etiology, based on the result of the aforementioned analysis; and determining if this loss is due to a reduced and/or limited neural response, which induces alterations in the innervation of the intrinsic ocular muscles of the eye.

8 Claims, No Drawings

METHOD FOR THE DETECTION OF VISUAL FUNCTION LOSSES

FIELD OF THE ART

The present invention relates in general to a method for detecting visual function losses from an optical quality analysis of retinal images and, in particular, to a method comprising carrying out said analysis relating to an eye with a healthy anterior segment and healthy intraocular media, and determining that the visual function loss is due to a reduced and/or limited neural response that induces alterations in the innervation of the intrinsic musculature of the eye.

STATE OF THE PREVIOUS ART

Methods for the detection of visual function losses are known from the analysis of the optical quality of a few retinal images.

A method and a system are proposed in EP2147633A1 for the measurement of the scattering of light in the ocular globe or region based on the recording and processing of retinal images free from the influence of low order aberrations so as to detect/diagnose pathologies in the anterior segment of the eye, such as cataracts, carry out the tracking of patients that have undergone refractive surgery or have been implanted with intraocular lenses or measure the quality of the tear of the eye.

It is proposed that, for one preferred embodiment of EP2147633A1, a ratio of an objective scatter index, known as OSI, be obtained that relates the light energy found in a peripheral area of the retinal image to the light energy found in a central area, and which allows measuring just the intraocular scattering, as opposed to other parameters, as, for instance, the commonly known Strehl index or ratio, which are global optical quality parameters that take into account both intraocular scattering and aberrations (if the information relative thereto is found in the image), without permitting an independent analysis thereof.

In EP2147633A1 it is not described or suggested that the proposed system and method be applied to the analysis of retinal images for the detection of visual function losses in eyes not suffering from pathologies in the anterior segment or the intraocular media.

The article "Retinal-Image Quality and Contrast-Sensitivity Function in Age-Related Macular Degeneration", by Carolina Ortiz, José R. Jiménez, Francisco Pérez-Ocón, José J. Castro and Rosario González-Anera, in *Current Eye Research*, 35(8), 757-761, 2010, proposes to analyse the quality of the retinal image in cases of age-related macular degeneration (ARMD).

Likewise, the article "New testing software for quantifying discrimination capacity in subjects with ocular pathologies", by José J. Castro, José R. Jiménez, Carolina Ortiz, Aixa Alarcón, and Rosario G. Anera, in *Journal of Biomedical Optics*, 16 (1), 015001 (January 2011) proposes new software for quantifying, through the analysis of the optical quality of retinal images, the discrimination capacity in patients with pathologies, including the retinal pathology known as age-related macular degeneration.

In both articles, the Strehl index is used for carrying out the measurement of optical quality, with the above-mentioned drawbacks regarding the impossibility of measuring intraocular scattering independently from aberrations, and their authors assume that the increase in intraocular scattering is due to the retina itself rather than the ocular medium, with "Retinal-Image Quality and Contrast-Sensitivity Function in Age-Related Macular Degeneration" explicitly indicating that the ocular medium of a patient affected by ARMD should not be deteriorated, because this pathology affects mostly the retina, but does not alter the properties of the cornea and/or the lens.

Neither of these articles proposes to determine that the poor optical quality of the retinal images may be due, at least in part, to a limited/relaxed neural response associated with a healthy anterior segment and/or healthy intraocular media.

DISCLOSURE OF THE INVENTION

Offering one alternative to the state of the art is deemed necessary covering the shortcomings found in the latter, in particular those due to the absence of proposals that will take into account the influence that a healthy anterior segment and/or healthy intraocular media can have in the poor optical quality of corresponding retinal images.

For such a purpose, the present invention relates to a method for detecting visual function losses comprising analysing the optical quality of a patient's eye from at least one retinal image thereof or from information related to said retinal image.

Unlike known methods, the one proposed by the present invention comprises carrying out said analysis on at least one retinal image of a healthy anterior segment (cornea) and healthy intraocular media (aqueous humour, lens and vitreous humour), the method comprising detecting, based on the result of said analysis, the functional aetiological or pathological visual function loss of the visual system, and determining that the latter is due to a reduced and/or limited neural response that induces alterations in the innervation of at least part of the intrinsic ocular musculature of said eye.

Said reduced and/or limited neural response causes the worsening of the ocular optical quality, which is detected through the analysis of retinal images according to the method proposed by the present invention.

According to exemplary embodiments, the method comprises determining that said alterations are induced in the innervation of one or more of the following muscles: ciliary muscle (causing accommodation limitations resulting in the loss of the accommodative efficacy and of focusing), iris dilator muscle or iris sphincter muscle, or any other muscles forming part of the intrinsic ocular musculature.

The method comprises determining that said reduced and/or limited neural response is due to a defective transmission of information from the retina to the brain (afferent pathway) or from the brain to the eye (efferent pathway), which causes the latter to give said reduced and/or limited response.

For one embodiment, representative of a first deductive path, the method comprises determining that said reduced and/or limited neural response is due to a pathological or structural alteration of the retina.

Depending on the variant of said embodiment, said pathological alteration in the retina is an alteration typical of the macular area, or it is not typical of the macular area but has macular implications or is relative to a pathology for which the fibres transmitting the visual information are altered and give rise to lesions limiting the information sent to the brain and/or received therefrom.

Said pathological alteration in the retina is due to:
  macular alterations, including at least one of the following alterations: maculopathies, central hole of the retina, central serous choriopathy, age-related macular degeneration or ARMD, or obstructions of the central retinal artery or its branches, or obstructions of the central retinal vein or its branches;

pathology of the subretinal membranes, or diabetic retinopathy or hypertensive retinopathy;

optic nerve pathologies, including at least one of the following pathologies: optic nerve atrophy, papilloedema, optic neuritis, anterior or posterior ischaemic optic neuropathy or glaucoma;

pathology of the visual pathway, including at least one of the following pathologies: lesions of the optic chiasm or in the optic tract fibres, or in the geniculate body, or in the parietal and temporal optic radiation fibres, or in the occipital area anterior, medial or posterior fibres;

any other causes associated with other types of retinal pathologies.

According to one further embodiment, representative of a second deductive path, the method comprises determining that the reduced and/or limited neural response is due to a functional alteration, in general functional amblyopia.

According to one variant of said embodiment, said functional alteration is the cause of partial or total cortical blindness unless it is properly treated.

In order to rule out that the visual function loss may be due to a pathology of the anterior segment and/or of the intraocular media, the method comprises determining that the anterior segment and the intraocular media are healthy, through an exploration thereof previously or subsequently to the analysis of the optical quality, carried out, for instance, with a biomicroscope, with optical coherence tomography or with ultrasonics echography.

According to one embodiment, the method comprises determining that the eye retina is healthy or suffers from a pathological or structural alteration, through an exploration of the retinal structures previously or subsequently to the analysis of the optical quality, determining, in case the retina is healthy, that the visual function loss is of a functional aetiological type, i.e., the above-referred second deductive path is applied.

In case that, from said exploration of the retinal structures, it is determined that the retina suffers from a pathological or structural alteration, the method of the present invention comprises complementing the results obtained through the analysis of the optical quality of retinal images with those obtained through said exploration so as to carry out a more precise diagnosis of the pathological or structural alteration of the retina.

The method of the present invention comprises carrying out said exploration of the retinal structures with a direct or indirect ophthalmoscope, with a retinography scan, with an angiography, with an optical coherence tomograph, with laser scan tomography, with a polarised laser scan or with any other apparatus that is deemed suitable, both in the present and the future, for such a purpose.

According to one embodiment, the method comprises obtaining the retinal image or images by carrying out the following steps:

projecting a pinpoint light beam into the retina of said patient's eye; and recording one or more images of the retina plane, or retinal images, resulting from the light reflected in the retina by said pinpoint light.

In one variant of said embodiment, the method comprises carrying out said steps with a double-pass ophthalmoscopic system.

In one embodiment, said analysis of the retinal image or images comprises analysing the contents related to intraocular scattering and aberrations or to just intraocular scattering.

The method comprises analysing the contents related to intraocular scattering, considering it as indicative of said optical quality, through the calculation of an objective scatter index, OSI, resulting from the relationship between the light energy found in a peripheral area of the retina plane image ($E_{ext}$) and the light energy found in a central area thereof ($E_c$), according to the expression:

$$OSI = \frac{E_{ext}}{E_c}$$

The teachings of EP2147633A1 are included, by reference, in the present application, both regarding the system used for the measurement of the scattering of light in the ocular globe or region and to the method proposed therein, excluding the embodiments relative to the various applications described therein (detection/diagnosis of pathologies in the anterior segment of the eye, such as cataracts, carrying out the tracking of patients that have undergone refractive surgery or have been implanted with intraocular lenses or measuring the quality of the tear of the eye).

According to one further embodiment, alternative or complementary of the previous one, the method comprises carrying out the optical quality analysis of the information related to the retinal image by measuring the aberration content of said information and utilising said measurement as a parameter indicative of optical quality.

In one particular implementation of said embodiment, the method comprises obtaining said information related to the retinal image and said measurement of the aberration content by means of an aberrometer (or other similar instruments), said information being derived from the wave function obtained through the aberrometer, as is the case of the information included in the PSF function ("Point Spread Function") derived from said wave function and which is related to the retinal image.

DETAILED DESCRIPTION OF EMBODIMENTS

In order to verify the merit of the method proposed by the present invention, a study has been carried out with one group of 30 eyes of 30 people with treated amblyopia and one control group of 43 eyes of 27 young and healthy people.

The average ages (±SD [range]) were 9.90±3.60 (8.62 to 10.93 years) for the amblyopic group and 7.13±2.56 (5.71 to 8.55 years) for the control group.

Double-pass retinal images were taken with a pupil diameter of 4 mm using a clinical instrument (OQAS, Visiometrics SL, Spain) (Güell et al. *J Cataract Refr Surg* 2004), and several parameters were computed related to the optical quality OQ and the intraocular scattering IS of the eye (Strehl index, OQAS values [OV] with 100%, 20% and 9% contrasts, and objective scatter index OSI) (Martínez-Roda et al. *Clin Exp Optom* 2011; Artal et al. Plos 2011).

In addition, the visual acuity, or BSCVA ("Best Spectacle-Corrected Visual Acuity"), was measured as corrected by the best spectacles with a standard logMAR graph.

The results obtained were as follows:

The LogMAR BSCVA for amblyopic eyes was 0.12±0.11, and −0.05±0.11 for the control group.

OQ and IS parameters:

for amblyopic eyes: Strehl index 0.19±0.08; 100% OV: 0.97±0.39; 20% OV: 1.03±0.47; 9% OV: 1.10±0.55; and OSI 1.34±1.11.

for the control group: Strehl index 0.25±0.07; 100% OV: 1.41±0.25; 20% OV: 1.49±0.36; 9% OV: 1.54±0.44; and OSI 0.58±0.20.

The results offered significant statistical differences ($p<0.05$) in most of the ocular quality parameters when amblyopic eyes were compared with those belonging to the control group, even in those that had already been treated and showing normal acuity values.

In the light of such results, it can therefore be concluded that smaller OQ and IS values have been found in amblyopic eyes as compared to those belonging to the control group. The visual acuity tests, however, did not show differences between the groups.

It is thus established that the method proposed by the present invention permits diagnosing function amblyopia in one eye with a healthy anterior segment and healthy intraocular media. A skilled artisan might introduce changes and modifications in the described embodiments without departing from the scope of the invention as defined in the attached claims.

The invention claimed is:

1. A method for detecting visual function losses, comprising:
    a) carrying out an exploration of an anterior segment and an intraocular media of an eye of a patient and determining, based on a result of said exploration, that both the anterior segment and the intraocular media of said eye are healthy;
    b) carrying out an optical quality analysis on at least one retinal image of said eye having a healthy anterior segment and healthy intraocular media as determined in step a) or from information related to said retinal image, wherein said optical quality analysis comprises analyzing the contents related to intraocular scattering and aberrations or to just intraocular scattering based on said retinal image, whereby the calculation of an objective scatter index, OSI, resulting from the relationship between the light energy found in a peripheral area of the retina plane image ($E_{ext}$) and the light energy found in a central area thereof ($E_c$), according to the expression:

$$OSI = \frac{E_{ext}}{E_c}$$

is considered as a parameter indicative of optical quality; and
    c) obtaining an indication of a functional aetiological or pathological visual function loss of the visual system depending on a result of said calculated OSI parameter.

2. The method according to claim 1, wherein said exploration of the anterior segment and the intraocular media of said eye is carried out with a technique selected from the use of a biomicroscope, optical coherence tomography or ultrasonics echography.

3. The method according to claim 1, further comprising determining that the retina of said healthy eye suffers from a pathological or structural alteration by means of an exploration of said anterior segment and intraocular media subsequent to said optical quality analysis.

4. The method according to claim 3, wherein said exploration of the retina is performed with a technique selected from the use of a direct or indirect ophthalmoscope, a retinography scan or an angiography, optical coherence tomography, laser scan tomography or a polarized laser scan.

5. The method according to claim 1, wherein said at least one retinal image of step b) is obtained by carrying out the following steps:
    projecting a pinpoint light beam into the retina of said patient's eye; and
    recording at least one image of the retina plane, or retinal image, resulting from the light reflected in the retina by said pinpoint light.

6. The method according to claim 5, further comprising: carrying out said steps with a double-pass ophthalmoscopic system.

7. The method according to claim 1, further comprising: carrying out the optical quality analysis of said information related to the retinal image of step b) by measuring the aberration content of said information to thereby obtain a measurement and utilizing said measurement as a parameter indicative of optical quality.

8. The method according to claim 7, further comprising: obtaining said information related to the retinal image and said measurement of the aberration content by means of an aberrometer, said information being derived from the wave function obtained through the aberrometer.

* * * * *